United States Patent [19]

Cramer

[11] 4,223,670
[45] Sep. 23, 1980

[54] RESTRAINT FOR USE IN PERFORMING A LUMBAR PUNCTURE

[76] Inventor: Judith C. Cramer, R.R. #1, Yoder, Ind. 46798

[21] Appl. No.: 965,292

[22] Filed: Dec. 1, 1978

[51] Int. Cl.³ ............................................. A61F 13/00
[52] U.S. Cl. .................................... 128/134; 269/328
[58] Field of Search ............. 128/133, 134, 94, 303 R; 269/328

[56] References Cited

U.S. PATENT DOCUMENTS

| | | | |
|---|---|---|---|
| 2,577,177 | 12/1951 | Anderson | 269/328 |
| 2,764,150 | 9/1956 | Ettinger et al. | 269/328 |
| 2,851,033 | 9/1958 | Posey | 128/134 |
| 3,829,079 | 8/1974 | Fox | 269/328 |

Primary Examiner—Lawrence W. Trapp
Attorney, Agent, or Firm—Ronald D. Welch

[57] ABSTRACT

A restraint for use in performing a Lumbar Puncture procedure on a pediatric patient, the restraint including a flexible panel having a plurality of portions, openings and straps for securing predetermined parts of a patient's body and securely holding same immobilized in a forwardly arched position with the subject's back fully exposed.

13 Claims, 9 Drawing Figures

RESTRAINT FOR USE IN PERFORMING A LUMBAR PUNCTURE

BACKGROUND OF THE INVENTION

1. Field of the Invention

The present invention relates to a restraining device for use in performing a spinal tap or lumbar puncture procedure and in particular to a garment-like restraint for engaging predetermined portions of a subject's body and securely immobilizing the subjects body in a forwardly arched position, the back of the subject being exposed.

2. Description of the Prior Art

The lumbar puncture procedure, more commonly refered to as a "spinal tap" and in which a small sample of spinal fluid is taken from the patient is a valuable diagnostic test procedure. This procedure is, however, painful. Simultaneously, during the performance of this procedure it is essential that the patient remain quite still. This is to avoid injury to the patient by reason of a bent or broken needle caused in turn by movement of a patient during the procedure, and to obviate a traumatic tap and the drawing of a bloody test sample which can render the test of little or no value.

Since a local anesthetic is rarely used, the difficulties in performing this procedure are further compounded when the procedure is performed on pediatric patients. It is therefore, necessary to have a nurse or other trained personnel present during the performance of the procedure to physically maintain the patient in a proper and essentially immobile position. Such a method is not entirely effective do to the quickness, strength, and unexpected movements of the pediatric patient. Correspondingly, use of trained personnel to physically restrain pediatric patients requires not only the presence of an additional person, it is also less than totally effective.

It has been proposed to provide a padiatric restraining device for securely holding the pediatric patient immobile during the spinal tap procedure. Such a device, for example, is manufactured by Olympic Medical Corp. 4400 7th South, Seattle Washington and is called an L P seat. This device includes a seat, rigid frames, and a mechanical harness. The device further holds the pediatric patient in an upright position during the procedure, this position not being desirable during the performance of this procedure, (a horizontal position being preferred).

There is, therefore, a need for a simple yet effective restraining device which may manufactured of a flexible material such as fabric, reinforced paper or plastic.

SUMMARY OF THE INVENTION

Broadly, the invention is a garment-like restraint for restraining a patient from movement during the spinal tap procedure.

The restraint includes an elongated panel provided with a plurality of openings for the head, shoulders, and legs of a patient and a plurality of straps which cooperate to securely yet comfortably engage selected portions of the patients body and to hold the patient immobile.

More specifically, the invention comprises an elongated and flexible panel having front and back surfaces and including upper tension, torso, thigh and lower tension portions, shoulder openings, upper thigh openings and a lower thigh opening formed in the panel between the upper tension and torso portions, between the torso and thigh portions, respectively. Laterally extending shoulder straps are fixedly secured to the panel adjacent the shoulder openings; buttocks and shin straps are fixedly secured to the panel in lateral extending spaced-apart relationships adjacent the upper thigh opening. The restraint is placed on the subject with the back surface of the torso portion against the front of the subjects torso, the subjects thighs passing through the upper thigh opening from the back surface to the front surface thereof. The subject's shoulders extend through the shoulder openings in a direction from the rear of the panel to the front thereof, and the buttocks and the shoulder straps are adjustably secured around and behind the subjects buttocks and shoulders, respectively. The upper and lower portions are drawn together forwardly of the torso portion to draw the subject into a forwardly arched position. The tension portions are adjustably secured together to hold the subject in this position.

Lastly, shin straps are secured around the front of the subjects lower legs or shins.

In one embodiment of the invention, the patients head may be restrained in a forwardly and downwardly extended position by the upper tension panel or in the alternative, may be extended in an unrestrained position through the forward tension panel via the head and neck openings provided therein.

In another specific embodiment of the invention, pockets are formed in the forward surface of the torso portion of the panel for recieving the patients hands. Wrist engaging straps are secured to the torso panel adjacent the pockets. The wrist straps are secured to hold the patients hands within the pockets to prevent the patient from using their hands to remove the restraint or otherwise move their arms and hands to produce undesired movement during the procedure.

It is therefore an object of the invention to provide a restraint for use in immobilizing a pediatric patient during the performance of the lumbar puncture procedure.

Another object of the invention is to provide such a restraint of a garment-like character which is easily fitted to a patient.

Still another object of the invention is to provide such a restraint which does not require the use of an additional trained person to physically restrain the patient to prevent undesired movement of the patient during the spinal tap procedure.

Another object of the invention is to provide such a restraint which includes means for immobilizing the movement of the hands and the arms of the patient.

Another object of the invention is to provide such a restraint which selectively permits restraining movement of the head of the patient.

Still another object of the invention is to provide such a restraint made from a fabric-like material.

Yet another object of the invention is to provide such a restraint which is readily adjustable to patients of different sizes.

Another object of the invention is to provide such a restraint in which adjustment of size is an integral part of placing the restraint on the patient.

Another object of the invention is to provide such a restraint which can be fabricated of a disposable fabric-like material.

Another object of the invention is to provide such a restraint which securely immobilizes the pediatric patient in a forwardly arched position with the back portion of the patient exposed.

BRIEF DESCRIPTION OF THE DRAWINGS

The above mentioned and other features and objects of this invention and the manner of attaining them will become more apparent and the invention itself will be best understood by reference to the following description of an embodiment of the invention taken in conjunction with the accompanying drawings wherein.

DESCRIPTION OF THE PREFERRED EMBODIMENT

Figure 1:
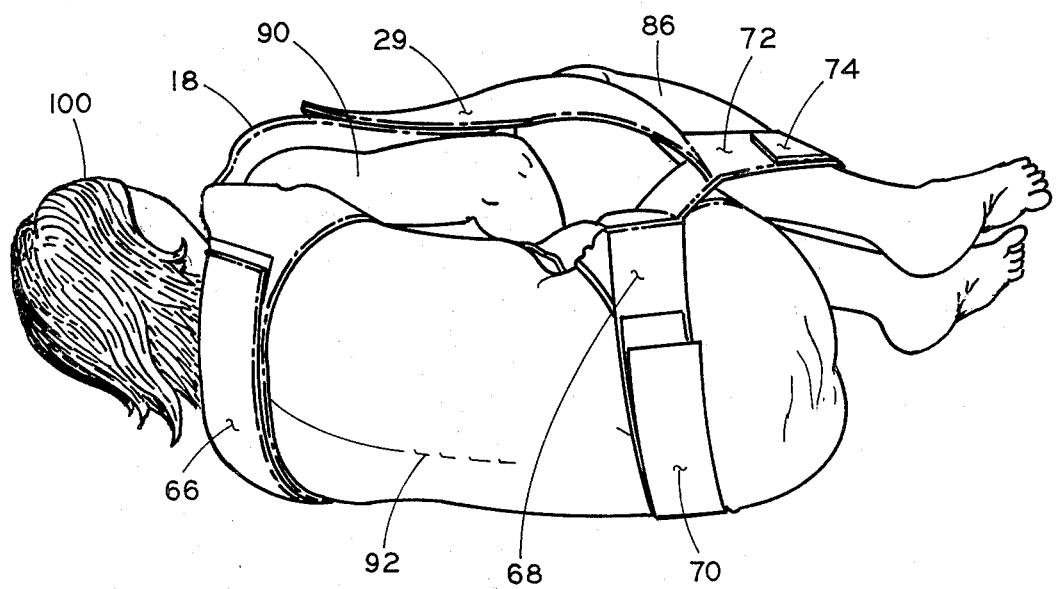
FIG. 1 is a perspective view showing the restraint of the present invention placed on a pediatric patient.
Figure 2:
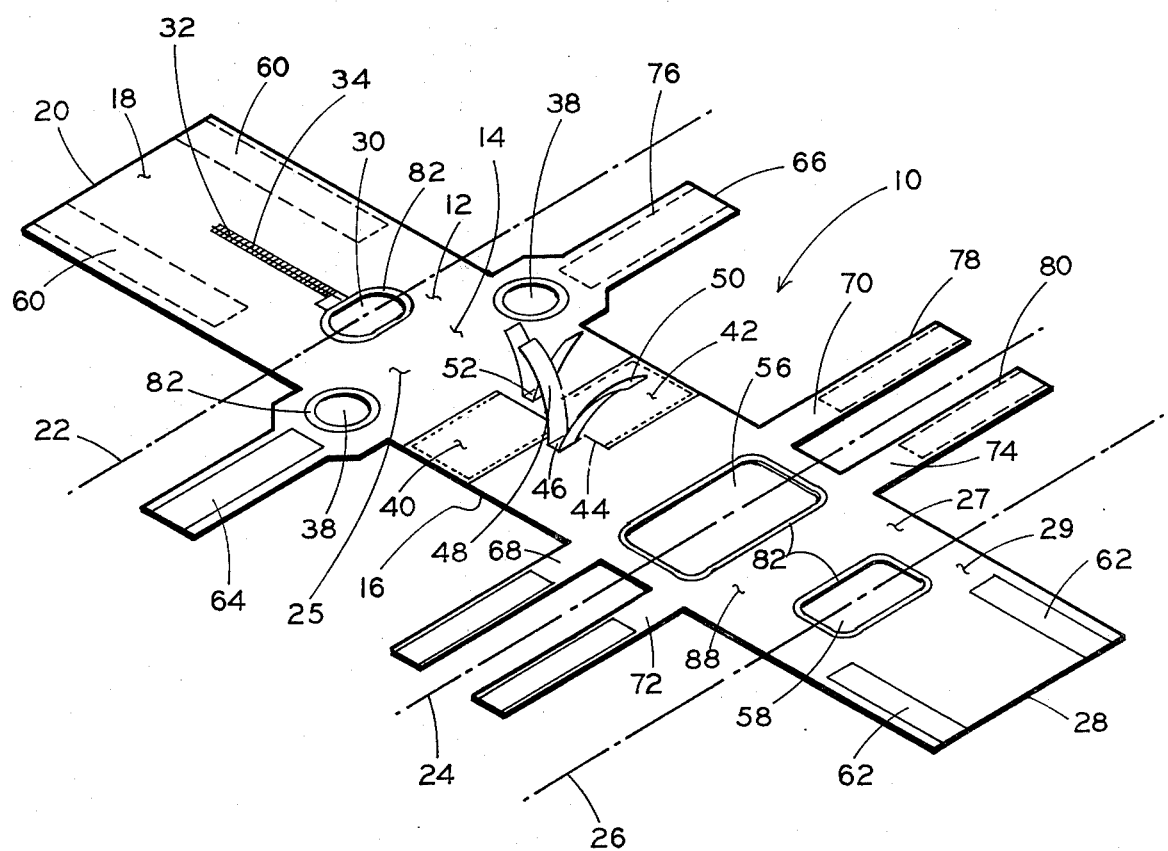
FIG. 2 is a perspective view of the restraint of the present invention which has been laid flat for identification of the panel portions.

Referring now to the drawings, there is shown a restraint in accordance with the present invention indicated generally at 10. The restraint 10 comprises an elongated, rectangular panel 12 which is fabricated from a strong stretch resistant and flexible material such as cotton denim. The panel 12, has a front surface 14 and a back surface 16. As viewed in FIG. 2, the left end portion of the panel 12 is identified as the upper tension portion 18, this portion extending from the end 20 of panel 12 to the dashed junction line 22. The portions of panel 12 between dashed junction lines 22 and 24 is identified as the torso portion 25, the portion between lines 24 and 26 as the thigh portion 27, and the portion between lines 26 and 28 as the lower tension portion 29.

A neck opening 30 is formed in the panel 12 at the juncture of upper tension panel 18 and torso portion 25, opening 30 being dimensioned to comfortably receive the neck of a child therethrough but smaller than a childs head.

An elongated slit 32 extends through opening 30 in a direction towards ends 20, slit 32 being provided with a conventional zipper 34 which, as will be explained below, permits the opening 30 to be enlarged to permit the passage of a patients head therethrough and then closed to prevent the patient from removing their head from the opening.

Shoulder openings 36, 38 are formed in the torso portion 25 adjacent junction line 22, openings 38 being disposed in laterally spaced-apart relationship and being dimensioned to receive the childs shoulders therethrough. A pair of pockets 40, 42 are stiched to the front surface 14, of panel 12 near the center of torso portion 25. Pockets 40, 42 are stiched along the side and outside ends, the inwardly disposed end 44 of pockets 40, 42 being open to permit the patients hands to be comfortably received therein.

An elongated strap 46 is fixedly secured to the front surface 14 of torso portion 25 adjacent the center of open end 44 of pocket 42 by means such as stitching. The opposite ends, 48, 50 of strap 46 are fitted with complementary Velcro material such that the straps can be secured around the wrist of the patient when the patients hand is in pocket 42. Similarly, a strap 52 is secured adjacent the center of open end of pocket 40.

An upper thigh opening 56, is formed adjacent the juncture line 24 of torso portion 25 and the thigh portion 27, opening 56 being dimensioned to comfortably recieve the childs thighs therethrough.

The upper tension portion 18 and lower tension portion 29 are provided with elongated strips of Velcro material as at 60, 62 respectively. The strips 60 on the upper tension panel are secured to the back surface 16 of the panel 12 while the strips 62 are secured to the front surface 14 thereof, strips 60 and 62 being of complementary Velcro material such that, and will again be explained in more detail below, the upper and lower tension panels can be adjustably secured together and overlying relationship.

The elongated shoulder straps 64, 66 extend laterally outwardly from the left (as viewed in FIG. 2) end of torso portion 25, straps 64, 66 being laterally in alignment with the shoulder strap openings 38.

Buttocks straps 68, 70 and shin straps 72, and 74 similarly extend laterally outwardly from panel 12 adjacent junction line 24. It will be observed that each pair of straps 64, 66, 68, 70, and 72, 74 is provided with a Velcro material fastening strip on its upper (as viewed in FIG. 2) surface, the opposite ones of each of these pairs of straps being provided with a complementary strip of Velcro fastening material on the under-surface as indicated by dashed lines at 76, 78 and 80 such that the strips can be adjustably secured together in overlying relationship.

Preferably, a padded welting as at 82 is stitched to the peripheries of the neck, shoulder, and lower thigh openings 30, 38, 56, and 58.

Figure 3:
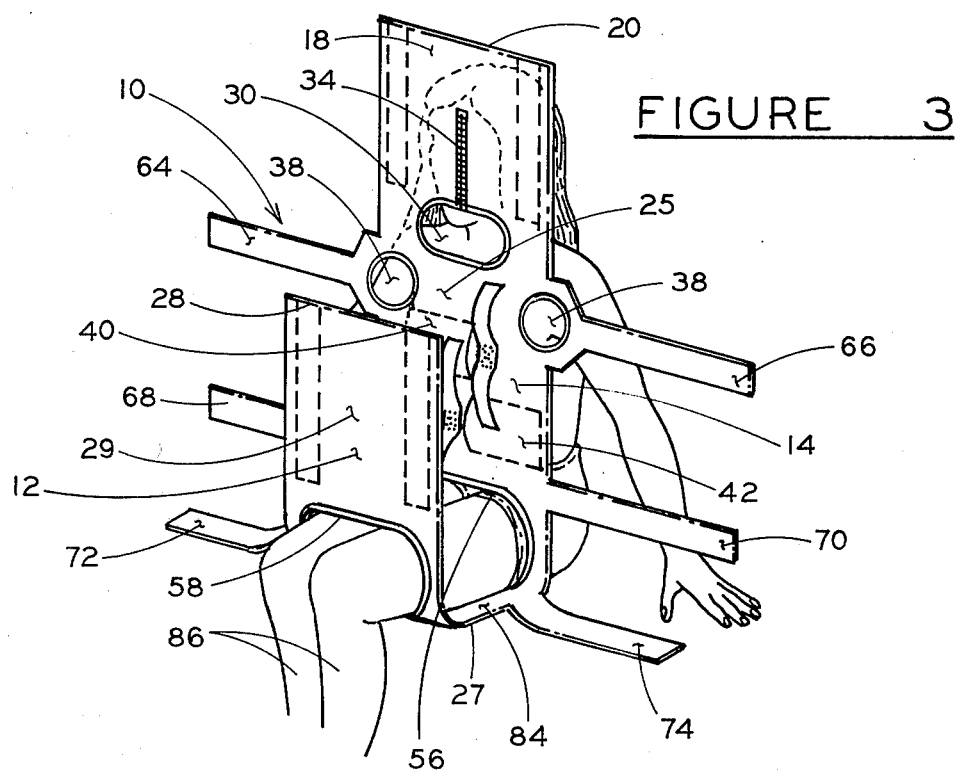
FIG. 3 is a perspective drawing illustrating the first step in the sequence of steps in placing the restraint on the patient.

Referring next to FIG. 3, there is illustrated the first step in placing the restraint 10 on the patient. The patients legs 86 are passed sequentially through the upper and then the lower thigh openings 56, 58 with the legs entering the upper thigh opening 56 from the rear surface 16 of panel 12, passing over the upper surface 88 of thigh portion 27 and entering the lower thigh opening 58 from the front surface 14 of panel 12. Thus positioned, the torso portion 25 passes vertically upwardly in front of the patients torso overlying the abdomen and chest with the pockets 40, 42 being disposed on the front surface 14 of panel 12 away from the patients body. The lower tension panel 29 extends upwardly and forwardly (with respect to the patients body) of the torso portion 25.

Figure 4:
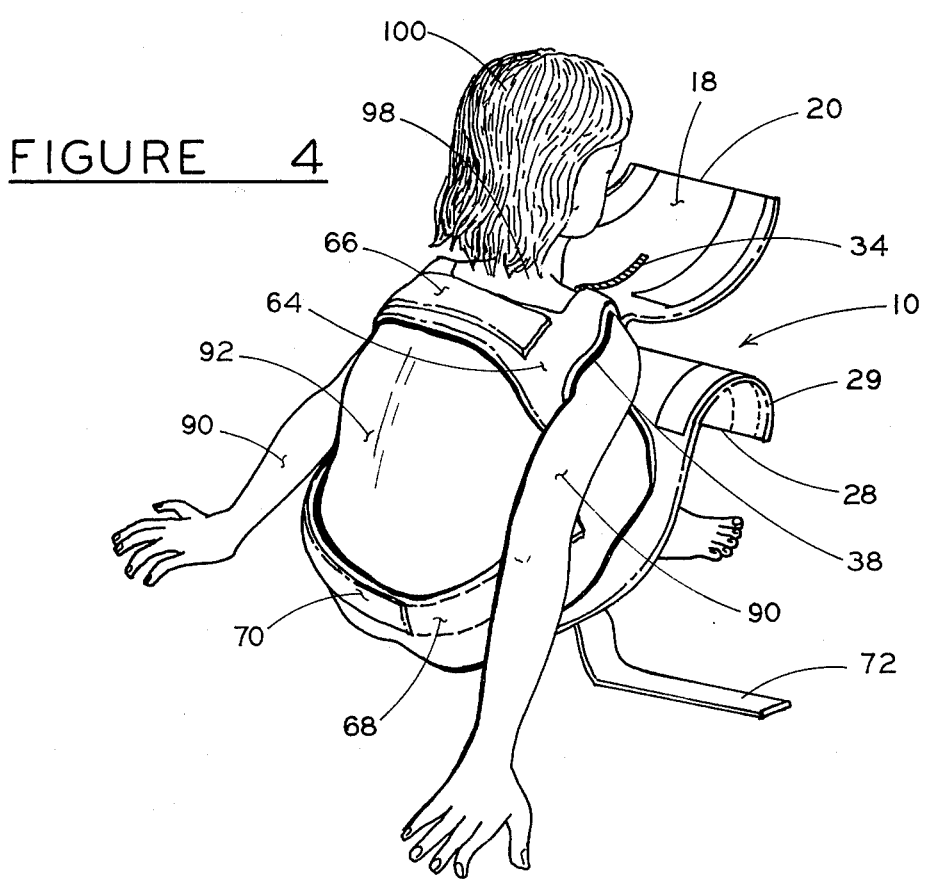
FIG. 4 is a perspective illustration of the second step in placing the restraint on the patient.

Referring next to FIG. 4, placement of the restraint 10 on a patient continues by placing the patients shoulders 90 through the shoulder openings 98 and securing the shoulder straps 64, 66 together snugly across the patients back 92. It will be apparent that the elongated Velcro strips 76 enable adjustment of the straps to any patient with a minimum of effort. In a similar manner, the buttocks straps 68, 70 are secured and snugged behind the buttocks adjacent the lower back.

Figure 5:
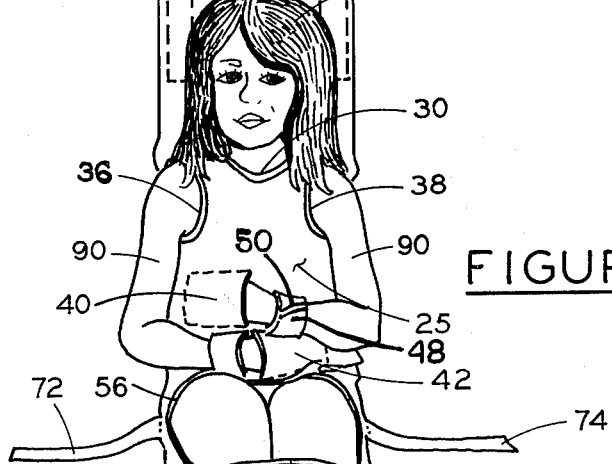
FIG. 5 is a perspective view showing placement of the patients hands to prevent movement.

Referring now to FIG. 5, the next step in placing the restraint 10 on the patient is to place the patients hands into pockets 40, 42. The patient's hands are retained in the pockets by securing the Velcro straps 48, 50 and 52 about the patient's wrists. This prevents the patient from moving his or her hands from the pockets 40, 42.

The upper and lower tension portions 18, 29 are now drawn together in overlapping relationship. Sufficient force is applied to urge the patient into a forwardly arched position and the two tension panels 18 and 29 are secured by means of the Velcro strips 60, 62.

If it is desired to leave the patient's head free, the final step in placing the restraint 10 on the patient includes the steps of placing the patient on his or her side, securing the lower portion of the patients legs 96 by securing the shin straps 72, 74 forwardly and around the lower legs or shins.

The patient is now positively and safely immobilized in a proper horizontal and forwardly arched position for performance of the spinal tap procedure.

Figure 7:
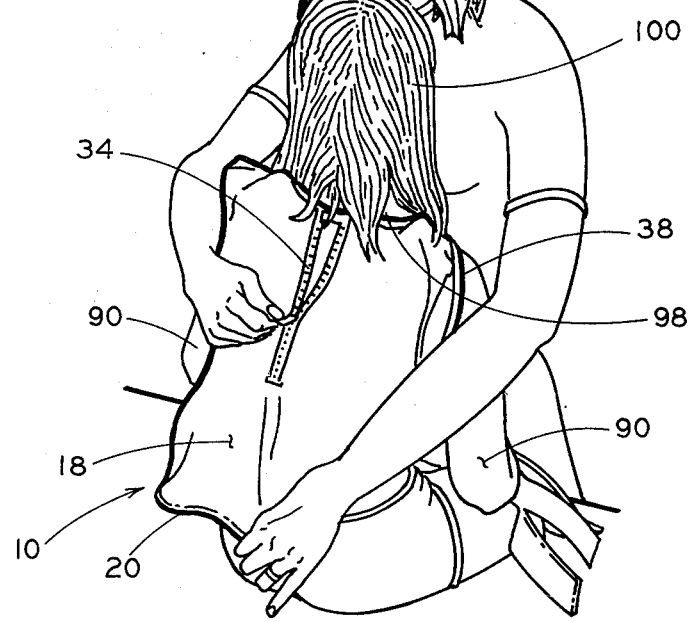
FIG. 7 is a perspective view showing the next sequential step in placing the restraint on the patient when it is desired to restrain the patients head movements.
Figure 8:
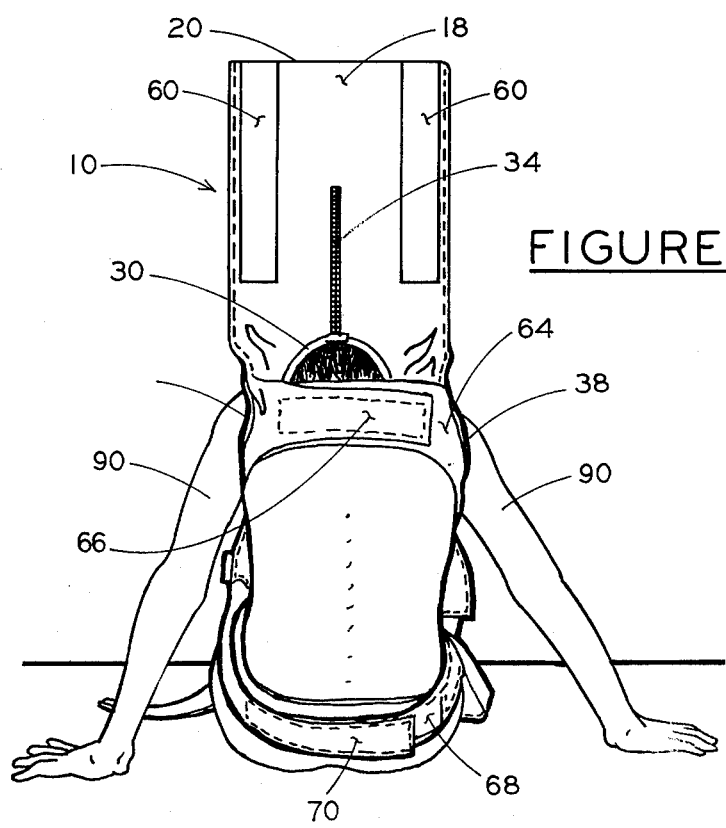
FIG. 8 further illustrates placing the garment on a pediatric patient when the head restraining feature is utilized.

In some instances, and in particular when the restraint is used on small children, it may also be desired to restrain movement of the head. To effect this, and as can best be seen in FIG. 7 and 8, the zipper 34 closing the slit 32 is opened and the upper restraining portion 18 is drawn over the patients head and neck with the head passing through opening 30. The zipper 34 is now closed thereby fitting the neck opening 30 snuggly about the patient's neck 98. The upper tension panel 18 can now be drawn up and over the patient's head as can best be seen in FIG. 8. The upper and lower tension panels are again drawn together in overlying relationship with enough force to draw the patient into a forwardly arched position. In this instance, it will be seen that the patient's head 100 is gently forced downwardly with the chin adjacent the chest and is prevented from movement by upper tension panel 18. Again, the child or patient is in a horizontal position with the entire back portion 102 and spinal column being fully exposed for performance of the spinal tap procedure.

Figure 6:
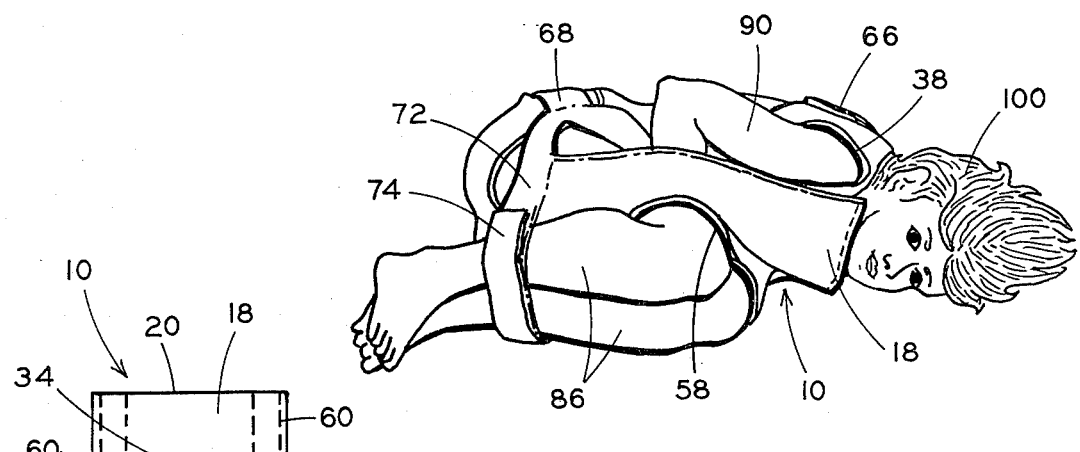
FIG. 6 is a front perspective view in illustrating the final step of placing the garment on the pediatric patient when the head of the patient is to be permitted to move.
Figure 9:
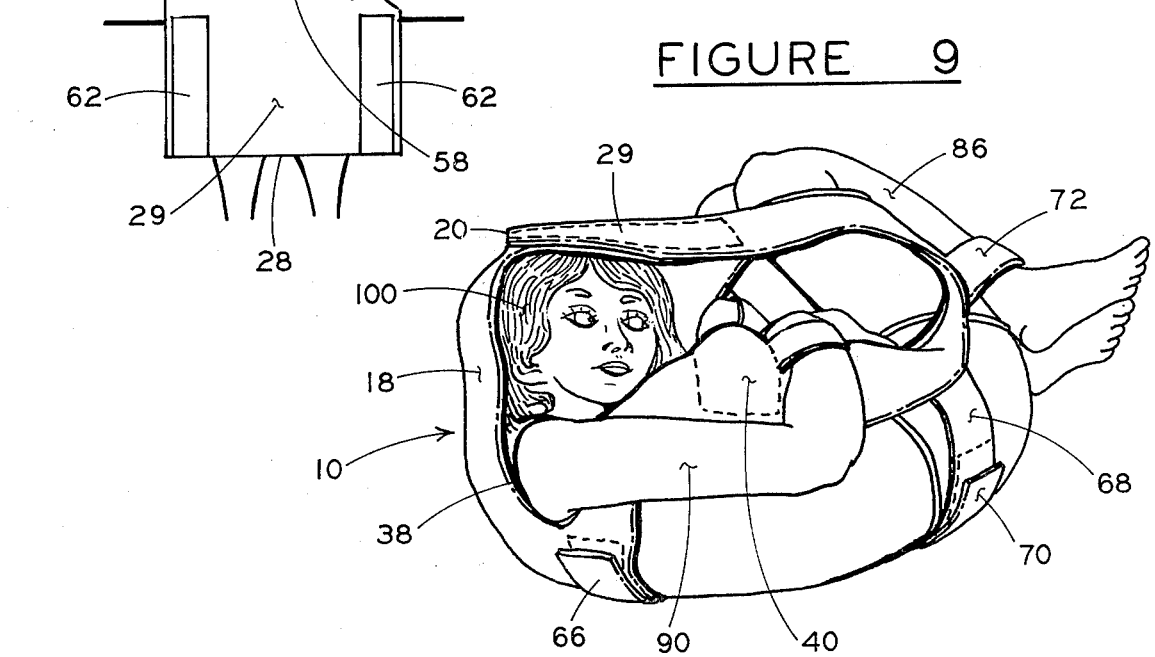
FIG. 9 is a rear perspective view showing the patient with the restraint fully placed thereon.

It will be further observed that since the restraint is fabricated entirely of a flexible fabric material, no discomfort is caused by cold metal or plastic surfaces. Bruising or other irritation of the body is obviated. The restrained position of the patient is not unduly uncomfortable and the patient, both with the head exposed and restrained as shown in FIGS. 9 and 6, respectively, is able to see. It will be observed that with the child thus restrained, a doctor can perform a lumbar puncture or a spinal tap with substantially increased ease and safely. The child is more effectively restrained from movement than can be effected by manually holding the child by a nurse or other trained personnel.

It is anticipated that the restraint can be fabricated in a minimum number of sizes in view of the adjustment available from the use of elongated Velcro strips for securing the garment. It is however, also contemplated that the entire restraint can be fabricated from a fiber reinforced paper-like material having sufficient strength. The Velcro strips can be replaced with suitable adhesive strips protected from sticking prior to use by conventional removeable plastic or waxed paper elements. Using such materials, the restraint can be made disposable for purposed of sterility and cleanliness without loss of its effectiveness and without imposing undue expense. It will further be observed that while a particular geometric configuration of the elongated panel has been illustrated, the fundamental physical and functional characteristics of the restraint can be effected using varied geometry. In the broad aspects of the invention, is is necessary only that flexible shoulder and thigh engaging means be provided, these being adjustably coupled together forwardly of the patient's body to securely hold the patient in an immobile and forwardly arched position.

While there have been described above the principles of this invention in connection with specific apparatus, it is to be clearly understood that this description is made only by way of example and not as a limitation to the scope of the invention.

What is claimed is:

1. A restraint for use in performing a lumbar puncture procedure; an elongated, flexible panel having front and back surfaces and including upper tension, torso, thigh, and lower tension portions, shoulder openings, an upper thigh opening, and a lower thigh opening being formed in said panel between said upper tension and torso portions, between said torso and thigh portions, and between said thigh and said lower tension portions, respectively, laterally extending shoulder straps fixedly secured to said panel adjacent said shoulder openings, buttocks and shin straps fixedly secured to said panel in laterally extending, spaced-apart relationship adjacent said upper thigh opening, the restraint being placed on said patient with the back surface of said torso portion against the front of said subject's torso, the subject's thighs passing through said upper thigh opening from the back surface of said panel, over the front surface of said portion, and through said lower thigh opening in a direction from the front to the back surface of said panel, said buttocks and said shoulder straps being secured around subjects buttocks and shoulders, respectively, said shin straps being secured around the subject's shins securing same adjacent said patients thighs, said upper and lower tension panels being drawn together forwardly of said torso portion to draw the subject into a forwardly arched position and secured to thereby hold said patient immobilized in said forwardly arched position.

2. The restraint of claim 1, further including a neck opening formed in said upper tension portion adjacent the juncture of said upper tension and torso portions, and means for selectively enlarging said neck opening, whereby, the patients head may be passed through said neck opening when is said enlarged condition thereof in a direction from the back surface of said panel to the front thereof, said enlarging means being selectively closed to secure said patients neck in said neck opening and said upper tension panel overlying and restraining movement of the patients head.

3. The restraint of claim 1, further including means for adjusting the secured length of said upper and lower tension panels to thereby permit adjustment of the forwardly arched position of said patient.

4. The restraint of claim 1, wherein each of said shoulder, buttocks, and shin straps includes oppositely disposed sections, and further including means for adjusting the secured lengths of said straps, said straps adjusting means including as elongated strip of complementary Velcro material secured longitudinally to opposite ones of each said pair of straps, said straps sections being secured together in selectively adjustable overlying relationship with the complementary Velcro material strips being pressed together to effect coupling.

5. The restraint of claims 3 or 4 wherein said means for adjusting the effective lentgh of said upper and lower tension panels includes elongated strips of complementary Velcro material longitudinally secured to opposite ones of said upper and lower tension panels in positions in registry one with the other when said upper and lower tension panels are disposed in overlying relationship.

6. The restraint of claim 1, further including pockets diminsioned to recieve a patient's hands therein, said pockets being fixedly secured to the front surface of said panel adjacent the center of said torso portion, each of said pockets having an open end, each said open end being oppisitely disposed to thereby recieve the right and the left hand of said patient therein, and further including a wrist strap fixedly secured to said torso portion adjacent the said open end of each said pocket for securing a patient's wrists when said patient's hands are in said pockets.

7. The restraint of claims 3 or 4 wherein said restraint is fabricated from a flexible, stretch-resistant material.

8. The restraint of claim 7, wherein said material is cottom denim.

9. The restraint of claim 8 wherein said restraint is fabricated from a flexible fiber-reinforced paper material, said means for adjusting the length of said straps and said means for securing said upper and lower tension panels including elongated strips of adhesive material fixedly secured to said straps and said tension panels in positions extending longitudinally thereof.

10. A device for restraining the movement of a patient comprising upper harness means for engaging the shoulders of a patient, lower harness for means of engaging the thighs of a patient, tension-strap means detachably coupled between said upper and lower harness means for selectively securing each to the other, to thereby restrain the patient in a forwardly arched position, and means for securing said patient's hands to said patient's torso.

11. A device of claim 10, wherein said upper harness means further includes means for securing said patient's head, against said patients chest when said upper harness means is secured to said lower harness means by said coupling means.

12. The device of claims 10 or 12, further including means coupled to said lower harness means for securing said patient's calves to said lower harness means.

13. The device of claim 10, further including means for selectively adjusting the length of said coupling means to thereby permit adjustment of said arched position.

* * * * *